(12) United States Patent
Larsen et al.

(10) Patent No.: US 11,832,949 B2
(45) Date of Patent: Dec. 5, 2023

(54) MONITORING SYSTEM COMPRISING A MASTER DEVICE IN WIRELESS COMMUNICATION WITH AT LEAST ONE SLAVE DEVICE HAVING A SENSOR

(71) Applicant: WIDEX A/S, Lynge (DK)

(72) Inventors: Soren Mollskov Larsen, Varlose (DK); Morten Kroman, Taastrup (DK)

(73) Assignee: WIDEX A/S, Lynge (DK)

( * ) Notice: Subject to any disclaimer, the term of this patent is extended or adjusted under 35 U.S.C. 154(b) by 538 days.

(21) Appl. No.: 16/712,230

(22) Filed: Dec. 12, 2019

(65) Prior Publication Data

US 2020/0187809 A1 Jun. 18, 2020

Related U.S. Application Data

(60) Provisional application No. 62/779,574, filed on Dec. 14, 2018.

(51) Int. Cl.
*A61B 5/291* (2021.01)
*H04W 4/80* (2018.01)
(Continued)

(52) U.S. Cl.
CPC ............ *A61B 5/291* (2021.01); *A61B 5/0024* (2013.01); *A61B 5/0082* (2013.01);
(Continued)

(58) Field of Classification Search
CPC . A61B 5/0024; A61B 5/02427; A61B 5/0082; A61B 5/291; A61B 5/6803;
(Continued)

(56) References Cited

U.S. PATENT DOCUMENTS

2004/0162035 A1* 8/2004 Petersen ................ A61B 5/002
455/404.1
2012/0289792 A1 11/2012 Jain et al.
(Continued)

FOREIGN PATENT DOCUMENTS

CN 101778405 B 1/2013
DE 10 2015 015 113 A1 5/2017
(Continued)

OTHER PUBLICATIONS

Communication dated Mar. 3, 2022 from the European Patent Office in EP Application No. 19211147.4.
(Continued)

*Primary Examiner* — Alex M Valvis
*Assistant Examiner* — Chanel J Jhin
(74) *Attorney, Agent, or Firm* — Sughrue Mion, PLLC

(57) ABSTRACT

A monitoring system including a master device adapted for wireless communication with at least one slave device having a sensor. The sensor of the at least one slave device is adapted for acquiring a physiological signal. The master device is adapted for providing a synchronization signal to the at least one slave device and instructing the at least one slave device to acquire the physiological signal based on timing instructions. The at least one slave device is adapted for acquiring the physiological signal by means of the sensor according to the received timing instructions and transmitting the acquired physiological signal wirelessly to the master device. The master device includes a processor for processing the synchronized, physiological signals acquired by sensors synchronized via wireless communication.

13 Claims, 5 Drawing Sheets

(51) Int. Cl.
*A61B 5/00* (2006.01)
*A61B 5/024* (2006.01)
*H04W 56/00* (2009.01)

(52) U.S. Cl.
CPC ........ *A61B 5/02427* (2013.01); *A61B 5/6803* (2013.01); *A61B 5/6817* (2013.01); *A61B 5/7203* (2013.01); *H04W 4/80* (2018.02); *H04W 56/00* (2013.01)

(58) Field of Classification Search
CPC ..... A61B 5/6817; A61B 5/7203; H04W 4/80; H04W 56/00
USPC ........................................................ 600/544
See application file for complete search history.

(56) References Cited

U.S. PATENT DOCUMENTS

| | | |
|---|---|---|
| 2014/0257058 A1 | 9/2014 | Clarysse et al. |
| 2015/0157220 A1 | 6/2015 | Fish et al. |
| 2015/0157262 A1 | 6/2015 | Schuessler |
| 2016/0255600 A1 | 9/2016 | Hayami et al. |
| 2017/0359162 A1 | 12/2017 | Granqvist et al. |
| 2018/0092554 A1 | 4/2018 | Zhang et al. |
| 2018/0225889 A1 | 8/2018 | Kolen et al. |
| 2018/0353086 A1 | 12/2018 | Turner et al. |
| 2019/0046121 A1* | 2/2019 | Khachaturian .... A61B 5/02055 |

FOREIGN PATENT DOCUMENTS

| | | |
|---|---|---|
| EP | 2 736 274 A2 | 5/2014 |
| EP | 2 967 366 A1 | 1/2016 |
| EP | 3 291 730 A1 | 3/2018 |
| WO | 2016/065476 A1 | 5/2016 |
| WO | 2018/013569 A1 | 1/2018 |
| WO | 2018/134380 A1 | 7/2018 |

OTHER PUBLICATIONS

Chi-Chun Chen et al., "A Tail-Worn Sensor-Equipped Heart Rate Measurement Apparatus for Ischemic Stroke Prevention", Department of Electronic Engineering, National Chin-Yi University of Technology, Taichung, Taiwan; Research Article—Neuropsychiatry, 2018, vol. 8, Issue 1.

Matej Marinko, "Continuous Blood Pressure Estimation from PPG Signal", Faculty of Mathematics and Physics, Jadranska cesta 19, 1000 Ljubljana; Informatica 42, 2018, vol. 33-42.

Hao Lin et al., "Noninvasive and Continuous Blood Pressure Monitoring Using Wearable Body Sensor Networks", Northeastern University, China; IEEE Intelligent Systems, Nov.-Dec. 2015, vol. 30, Issue: 6.

* cited by examiner

MONITORING SYSTEM COMPRISING A MASTER DEVICE IN WIRELESS COMMUNICATION WITH AT LEAST ONE SLAVE DEVICE HAVING A SENSOR

CROSS-REFERENCE TO RELATED APPLICATIONS

This application claims benefit of provisional application No. 62/779,574 filed Dec. 14, 2018, the disclosure of which is incorporated by reference herein.

The present invention relates to a monitoring system comprising a master device in wireless communication with at least one slave device having a sensor.

BACKGROUND OF THE INVENTION

Mobile devices, like a watch with sensors, are known as a fitness tracker. This is a device or application for monitoring and tracking fitness-related metrics such as distance walked or run, calorie consumption, and in some cases heartbeat and quality of sleep. The data is often loaded wirelessly into a computer or a smartphone for long-term data tracking.

Remote patient monitoring is a technology to enable monitoring of patients outside of conventional clinical settings (e.g. in the home), which may increase access to care and decrease healthcare delivery costs. Most monitoring systems have a common architecture consisting of four components: a sensor unit capturing physiological parameters and enables short-range wireless communication; a patient device wirelessly connected to the sensor unit, having a local data storage, and interfaces towards a healthcare provider; a centralized repository to store data sent from sensors, local data storage, diagnostic applications, and healthcare providers; and finally diagnostic application software developing treatment recommendations and intervention alerts based on the analysis of collected data. The sensors may include blood pressure cuff, pulse oximeter, and glucometer. The remote patient monitoring systems may be used for monitoring dementia, falls, diabetes, congestive heart failure, etc.

Multi-sensor measurements are challenging as the sensors needs to be connected via wires to obtain synchronized signals that can be processed together. Hereby, it will be easier to suppress noise present in the sensor signals and extract more details from the sensor data. It furthermore becomes possible to obtain various sensor signals from different part of the body and to use the various sensor signals as multiple input for complex signal processing. This is desirable as the diagnostic application software now includes Artificial Intelligence and Machine Learning.

The purpose of the invention is to provide synchronized physiologic signals from at least two independent sensors for subsequent processing.

SUMMARY OF THE INVENTION

The invention is Directed to a monitoring system comprising a master device adapted for wireless communication with two slave devices each having a sensor adapted for acquiring a physiological signal; wherein the master device is adapted for providing synchronization signals to the two slave devices, and instructing the two slave devices to acquire the physiological signal based on timing instructions; wherein the two slave devices are adapted for acquiring the physiological signal by means of the sensor according to the received timing instructions, and transmitting the acquired physiological signal wirelessly to the master device; and wherein the master device comprises a processor adapted for processing the synchronized, physiological signals acquired by sensors of at least two slave devices in order to extract a measure for a physiological parameter.

The invention is further directed to a method of operating a monitoring system comprising a master device adapted for wireless communication with two slave devices each having a sensor adapted for acquiring a physiological signal, wherein the method comprises steps of: providing synchronization signals to the two slave devices, instructing the two slave devices to acquire the physiological signal based on timing instructions for synchronization, acquiring the physiological signal by means of the sensor according to the received timing instructions, transmitting the acquired physiological signal wirelessly from the at least one slave device to the master device, and processing in the master device the synchronized, physiological signals acquired by sensors in the two slave devices in order to extract a measure for a physiological parameter.

The invention is still further directed to a slave device having a sensor adapted for acquiring a physiological signal, characterized in that the slave device is adapted for: receiving a synchronization signal wirelessly from a master device, extracting timing instructions from the synchronization signal, acquiring a physiological signal by means of the sensor based on the timing instructions, and transmitting timing metadata accompanied with the acquired physiological signal to the master device.

Preferred embodiments will be described below and are further defined in the dependent claims.

A remote patient monitoring system providing surveillance based on independent multi-sensor measurements, enables monitoring of patients outside of conventional clinical settings (e.g. in the home). The sensors may be shaped as hearing aids and thereby not influence the movements of the patient, and the quality of the monitored data may be comparable to clinical monitoring at hospital.

BRIEF DESCRIPTION OF THE DRAWINGS

The invention will be described in further detail with reference to preferred aspects and the accompanying drawing, in which.

DETAILED DESCRIPTION

Figure 1:
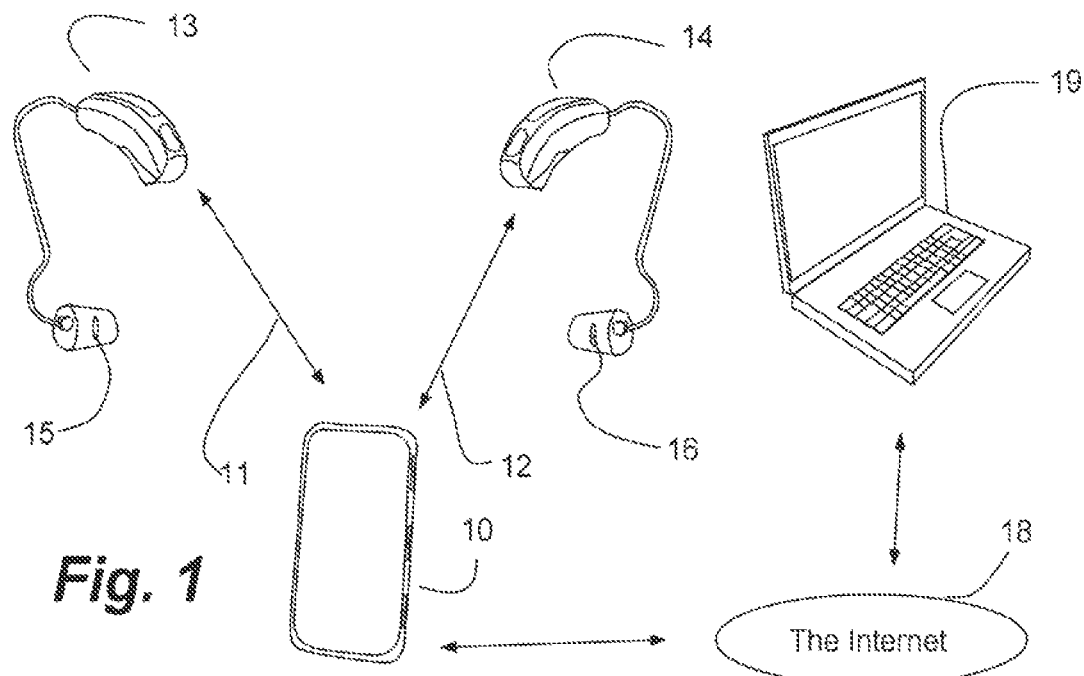
FIG. 1 illustrates one embodiment of master device and two sensor devices according to the invention.

FIG. 1 illustrates one embodiment of master device and at least two slave devices according to the invention. The master device and the two slave devices with sensors are arranged in a Wireless Body Area Network (WBAN) providing a monitoring system. In the present embodiment, the master device is embodied by a personal communication device 10, while the two slave devices are embodied by a set of hearing aids 13 and 14. The master device is adapted for wireless communication with the at least two slave devices (hearing aids 13 and 14). In one embodiment, the wireless communication takes place by means of wireless links 11 and 12 operating according to the Bluetooth Low Energy protocol.

In one embodiment, the two hearing aids 13 and 14 each comprise a sensor 15 and 16, respectively, adapted for acquiring a physiological signal. The sensors 15, 16 are in one embodiment PPG (photoplethysmogram) sensors. The PPG sensors 15, 16 obtains optically a plethysmogram which is a volumetric measurement of an organ. A PPG sensor is often used for obtaining a photoplethysmogram by using a pulse oximeter illuminating the skin and measures changes in light absorption. Such a pulse oximeter monitors the perfusion of blood to the dermis and subcutaneous tissue of the skin.

In one embodiment, the sensors 15, 16 are electrodes provided on ear molds for sensing an EEG signal from the ear canal of the hearing aid user.

In other embodiments, the sensors 15, 16 are accelerometers build in or attached to the ear molds.

The master device is adapted for providing a synchronization signal to the at least two slave devices, and for instructing the slave devices for triggering sensor for the acquisition of the physiological signal. The at least two sensors are adapted for acquiring the physiological signal according to the received timing instructions and for transmitting the acquired, synchronized physiological signal wirelessly to the master device. The master device comprises a processor for processing the synchronized physiological signal acquired by the at least two sensors.

According to one embodiment of the invention, the wireless, synchronized PPG sensors 15, 16 are configured as multi-site photoplethysmography (MPPG). Hereby, simultaneous measurements from e.g. the right and left ear lobes and/or other appropriate body parts may be carried out wirelessly. This will make it possible for medical professionals to assess patients with suspected peripheral arterial disease, arterial stiffness, autonomic or endothelial dysfunction. Multi-site photoplethysmography (MPPG) also offers significant potential for data mining, e.g. via deep learning, as well as a range of innovative pulse wave analysis techniques. In one embodiment useful in a medical care center, the sensor devices 13 and 14 are coupled via the master device 10 directly to a powerful computer 19 responsible for e.g. the deep learning calculations. In another embodiment useful for remote monitoring, the sensor devices 13 and 14 are coupled via the master device 10 and the Internet 18 to the powerful computer 19. The acquired, synchronized physiological signal wirelessly to the master device 10, and in one embodiment, the master device 10 uploads the acquired, synchronized physiological signal to the computer 19 for processing.

In cardiac cycles, the heart pumps blood to the body periphery. The pressure pulses are of course damped when reaching the skin but are sufficient to distend the arteries and arterioles in the subcutaneous tissue. When the pulse oximeter is placed against the skin (without compressing it), various characteristics may be observed, e.g. a pressure pulse caused by the venous plexus, as a small secondary peak.

The volume change caused by the pressure pulse generated by the heartbeat is detected by exposing the skin with the light from a light-emitting diode (LED) and measuring transmitted or reflected light by means of a photodiode. Hereby a peak may be observed for each cardiac cycle. The blood flow to the skin interfere with other physiological systems, why a PPG measurement can be used to monitor e.g. pulse, hypovolemia, blood pressure, breathing. Furthermore, the PPG waveform depends on the person observed, the location (arm, ear, finger) and how the pulse oximeter is attached to the body.

The pulsatile component of the cardiac cycle can be detected in a PPG measurement as the skin is so richly perfused. The PPG signal will have an AC component and a DC component. The DC component represents the bulk absorption of the skin tissue, while the AC component is directly representing variation in blood volume in the skin due to the pressure pulse.

The range of AC component of the PPG represents the difference between the systolic and diastolic pressure in the arteries. Physiological characteristics as premature ventricular contractions (PVCs), Ventricular tachycardia and ventricular fibrillation can also be detected from a PPG signal.

Figure 2:
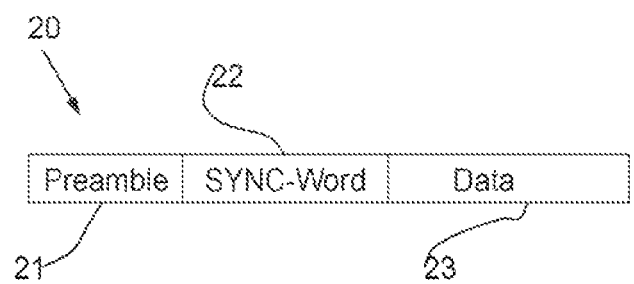
FIG. 2 illustrates the structure of a synchronization message sent from a master device to a sensor device according to one embodiment of the invention.
Figure 3:
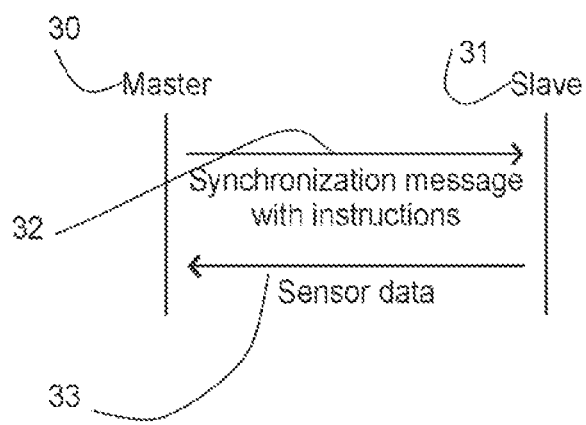
FIG. 3 illustrates the messaging structure between a master device and a sensor device according to one embodiment of the invention.

FIGS. 2 and 3 illustrate that a synchronization message 32 has a payload 20 including a preamble 21, a sync-word 22 and data bits 23. The synchronization message 32 is sent from a master device 30 to a sensor device or a slave device 31 according to one embodiment of the invention. The slave device 31 can detect the frequency of the signal and adjust its own clock frequency to the received signal by means of the preamble 21. The purpose of the clock frequency adjustment is essentially to find the center of the data bits. Furthermore, the preamble 21 is used to facilitate DC Compensation. In one embodiment, the preamble 21 is a fixed zero-one pattern of four symbols. The preamble is followed by the sync-word 22 which is used for determining the time of arrival of the first data bit and for estimating the time of later messages. In one embodiment, the sync-word 22 is a 64-bit code word preferably derived from the addresses of the devices involved in the communication. In one embodiment, the sync-word 22 is constructed to ensure a large Hamming distance between sync-words 22 used in different communications supervised by the master device 30. This provides good auto correlation properties of the sync-word 22 which improves timing acquisition. According to one embodiment of the invention the sync-word 22 is used to set a time anchor point by the slave device 31 to be used for synchronizing captured sensor signals returned to the master device 30. The data bits 23 are handled by the slave device 31, and the data bits 23 may include instructions to start capturing synchronized or time-stamped physiologic sensor signals and send the captured physiologic sensor signals in one or more data packets 33 to the master device 30.

In one embodiment, the instructions in the synchronization message 32 specify the timing when the slave device 31 must provide the response message containing the sensor data. By specifying to the individual slave devices 31 when to capture data and when to send data, the master device ensures that sensor data received from multiple sensors in multiple slave devices 31 are synchronized before data processing in the master device 30. This will also be valid when a sensor signal from an internal sensor (e.g. an accelerometer) in the master device 30 is included in the data processing.

Figure 4:
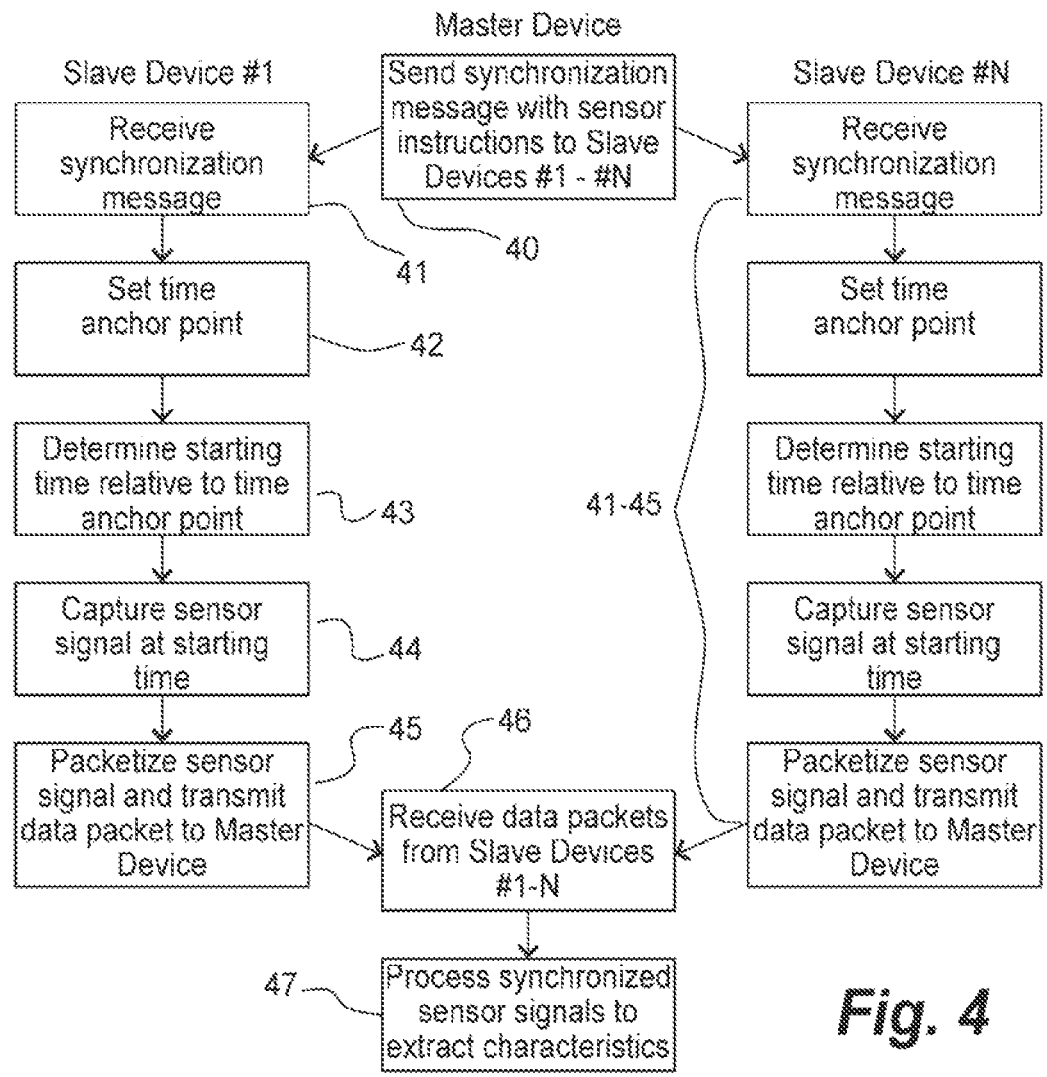
FIG. 4 shows a method for synchronizing sensor signal from wirelessly connected sensor devices according to the invention.

FIG. 4 shows a flow chart illustrating a method for synchronizing sensor signal from wirelessly connected sensing devices according to the invention. In step 40 a master device 30 sends a synchronization message 32 with instructions to one or more (#1-#N) slave devices 31. The first (#1) slave device 31 receives in step 41 the synchronization message 32, and in step 42 the slave device 31 sets a time anchor point based upon the excellent auto correlation properties of the sync-word 22. In step 43, the slave device 31, based on the instructions included in the synchronization message 32, determines the starting time set relatively to the time anchor point. According to the received instructions, the slave device 31 starts in step 44 to capture a sensor signal at a predetermined point of time relatively to the time anchor point. In step 45 the slave device 31 encodes the sensor signal into a digitized data packet and transmits this data packet to the master device 30. Normally the monitoring will require a continuous stream of digitized data packets transmitted to the master device 30. The slave device 31 will in the digitized data packets include timing metadata relevant for the signal processing in the master device 30. Each (#1-#N) of the slave devices 31 present in the sensor network will run through steps 41-45 and each transmit a continuous stream of digitized data packets to the master device 30. The master device 30 receives the continuous stream of digitized data packets from the slave devices 31 present in the sensor network in step 46. The master device 30 decodes the received data and timing metadata. In step 47, the sensor data collected at the plurality of distributed sensors in the plurality of slave devices 31 is processed centrally to extract characteristics from the sensor data. The master device 30 ensures that the captured data is synchronized.

Figure 5:
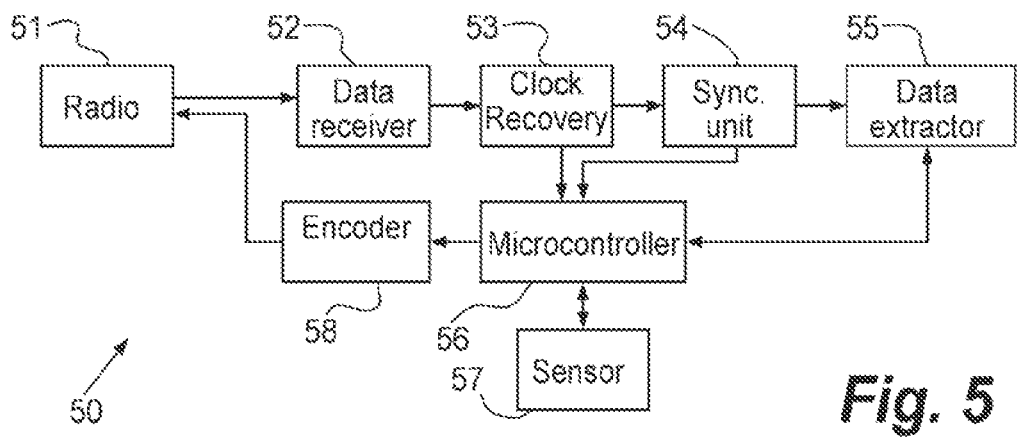
FIG. 5 illustrates the component of a sensor device according to one embodiment of the invention.

FIG. 5 illustrates the components of a slave device 50 or a sensor device according to one embodiment of the invention. The slave device 50 has a transceiver or a radio 51 for communication with a master device. The radio 51 may operate according to any suitable protocol, preferably a short-range radio protocol, e.g. the Bluetooth Low Energy protocol. A data receiver unit 52 receives the synchronization message 32 and isolates the payload 20 including the preamble 21, the sync-word 22 and data bits 23. A clock recovery unit 53 compares the system clock (not shown) of the slave device 50 to the received preamble 53, and a microcontroller 56 adjusts the system clock accordingly. A synchronization unit 54 includes an auto correlator where the incoming data is correlated with the predetermined sync word 22. A data extraction unit 55 receives the data bits 23 and communicates the instructions to a microcontroller 56. By means of the input from the synchronization unit 54 and the data extraction unit 55, the microcontroller 56 determines the starting for sensor signal acquisition, and controls a sensor 57, e.g. an accelerometer, accordingly. The microcontroller 56 packetize the captured sensor signal and transmits data packets to the requesting hearing device by means of an encoder 58 and the radio 51.

In one embodiment, the sync-word 22 is constructed to ensure a large Hamming distance between sync-words 22 used in different communications supervised by the master device 30. This provides good auto correlation properties of the sync-word 22 which improves timing acquisition.

For capturing physiologic signals, the intended use of the signal specifies the required sample rate. A normal resting heart rate for adult's ranges from 60 to 100 beats per minute. A lower heart rate at rest implies more efficient heart function and a good cardiovascular fitness, and for top-trained athletes a resting heart rate close to 40 beats per minute may be observed. For detecting the heart rate (the inverse of the Inter-Beat-Interval shown in FIG. 12), a sample rate of 25 Hz will be sufficient. For detecting parameters relating to the shape of the systolic point, the venous pulsation peak and the valley in between, a higher resolution will be required. Then a sample rate may be increased to 50 or 100 Hz or even higher. When measuring or monitoring the blood pressure, the vasoconstriction is measured which is the power difference between the diastolic point and the systolic point. In this use, a high precision will be required, and a 24-bit sample size or even higher may be applied.

In general, it is preferred to design sensors according to their intended purpose with predefined sample rate and sample size. The sensor will anyway have to have a stimuli unit, if required, and a capturing unit.

One embodiment according to the invention is based a sample size set to be 16 bits per sample. However, for certain purposes, larger sample sizes may be requested, e.g. 24-bit or 32-bit, which provides an almost infinite dynamic range, and only takes up twice as much storage as 16-bit samples.

Figure 6:
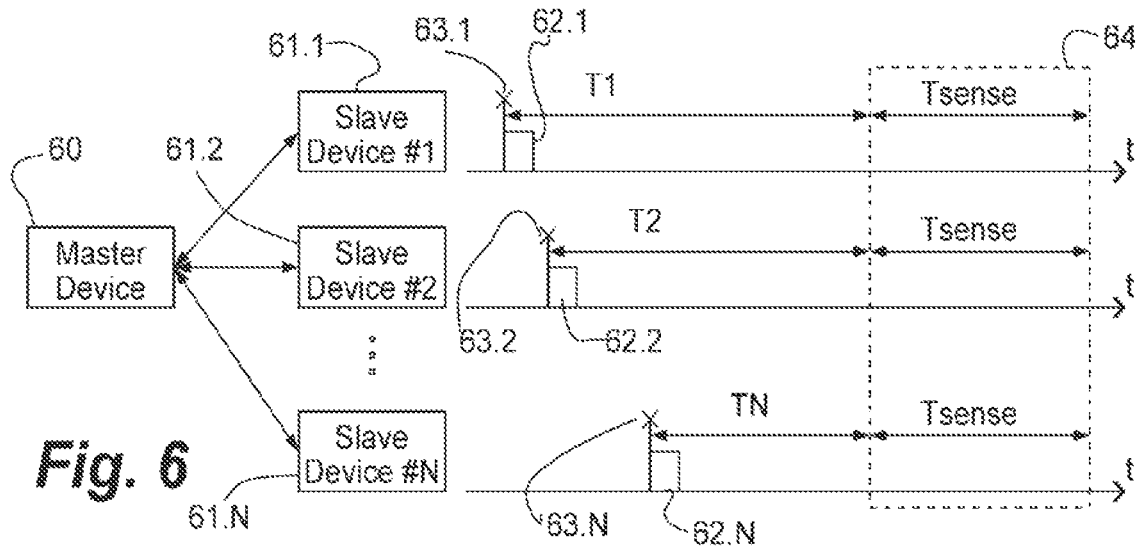
FIG. 6 illustrates how a plurality of devices are synchronized in one embodiment of a TDMA based wireless body area network according to the invention.

FIG. 6 illustrates how a plurality of devices are synchronized in one embodiment of a Time-division multiple access (TDMA) based wireless body area network according to the invention. At least one sensor device, here slave devices 61.1-61.N, is wirelessly connected to a master device 60.

Time-division multiple access (TDMA) is a channel access method allowing several devices to share the same frequency channel by dividing the signal into different time slots. The devices transmit in rapid succession, one after the other, each using its own time slot. This allows multiple devices to share the same radio frequency channel by using only a part of the channel capacity each. TDMA is based on a frame structure dividing a data stream into frames and further into time slots. A major advantage of TDMA is that the radio part of the devices only needs to listen and broadcast for its own time slot.

The master device 60 is in one embodiment responsible for the time slot allocation to the slave devices 61.1-61.N in the wireless body area network. The master device 60 sends a synchronization message 62.1 as explained with reference to FIGS. 2 and 3. The slave device 61.1 receives the synchronization message 62.1 and determines a time anchor point 63.1 as explained with reference to FIGS. 4 and 5. Furthermore, the slave device 61.1 determines from the payload of the synchronization message 62.1 the duration, Tsense, of a sensing period 64, and the time, T1, from the time anchor point 63.1 to the start of the sensing period 64. The other slave devices 61.2-61.N do the same. The only difference is that master device 60 managing the timeslot allocation in advance calculates the time, T1-TN, from the time anchor point 63.1-63.N to the start of the sensing period 64 individually of each of the slave devices 61.1-61.N and includes the individual time, T1-TN, in the payload of the synchronization messages 62.1-62.N for a particular slave device 61.1-61.N.

In this embodiment, the slave devices 61.1-61.N are addressed individually by the master device 60, as the slave devices 61.1-61.N each have a unique ID used for addressing purposes.

During the sensing period, the slave device 61.1-61.N captures respective sensor signals representing physiologic parameters, packetizes the captured sensor signals into payload of one or more data packets 33 (FIG. 3) to be sent to the master device 60 in respective allocated uplink time slots. After a number of data packets 33, it may be appropriate to resynchronize the individual slave device 61.1-61.N to the master device 60 why the master device 60 sends a new synchronization message 32 even though the data capturing is ongoing. The new synchronization message 32 does not have to contain data capturing instructions as it just serves synchronization purposes.

Figure 7:
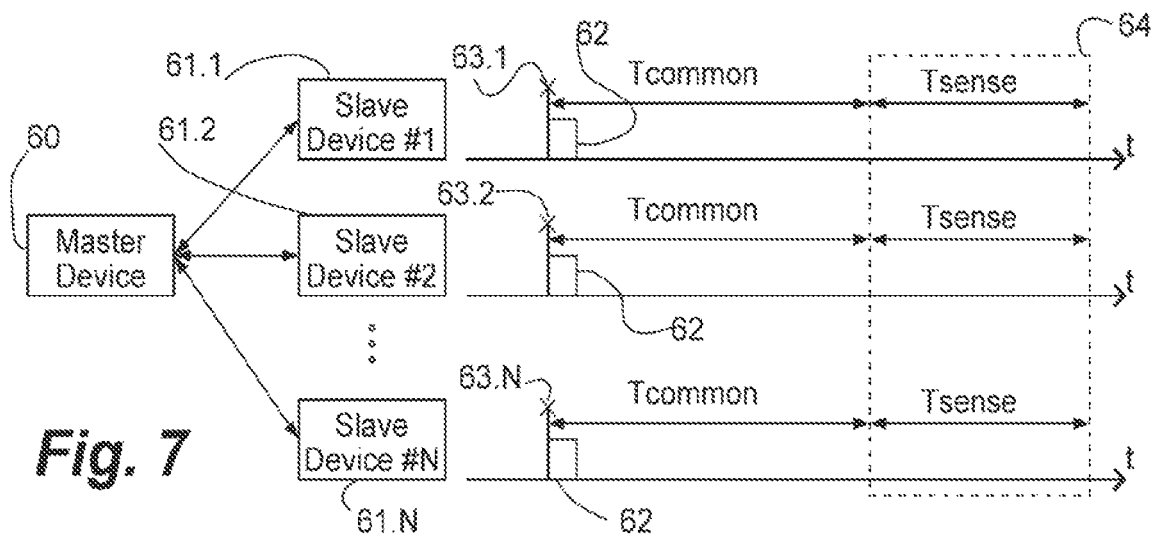
FIG. 7 illustrates how a plurality of devices are synchronized based on a broadcast message in one embodiment of a wireless body area network according to the invention.

FIG. 7 illustrates how a plurality of devices are synchronized based on a broadcast message in one embodiment of a wireless body area network according to the invention. At least one sensor device, here slave devices 61.1-61.N, is wirelessly connected to a master device 60.

The master device 60 is in this embodiment responsible for the timing in the wireless body area network. The master device 60 sends a synchronization message 62 as broadcasted message to the group of slave devices 61.1-61.N. Each of the slave devices 61.1-61.N receives the synchronization message 62 and determines a time anchor point 63.1-61.N as explained with reference to FIGS. 4 and 5.

Furthermore, the slave devices 61.1-61N determines the duration, Tsense, of a sensing period 64, and the time, Tcommon, from the time anchor points 63.1-63.N to the start of the sensing period 64. The time, Tcommon, is not critical as long as it is common for all the slave devices 61.1-61N. The time, Tcommon, may be communicated by the master device 60 or set for all the slave devices 61.1-61N in advance.

The slave devices 61.1-61.N, captures respective sensor signals representing physiologic parameters, and packetizes the captured sensor signals into payload of one or more data packets 33 (FIG. 3). In this embodiment, the slave devices 61.1-61.N may have a unique ID. The unique ID is not necessary for the broadcasted message 62 but is important when the slave devices 61.1-61.N send the packetized, captured sensor signals to the master device 60 in respective allocated uplink time slots or frequency channels. After a number of data packets 33, it may be appropriate to resynchronize the individual slave devices 61.1-61.N to the master device 60 why the master device 60 sends a new synchronization message 32 sent as a broadcasted message.

Figure 8:
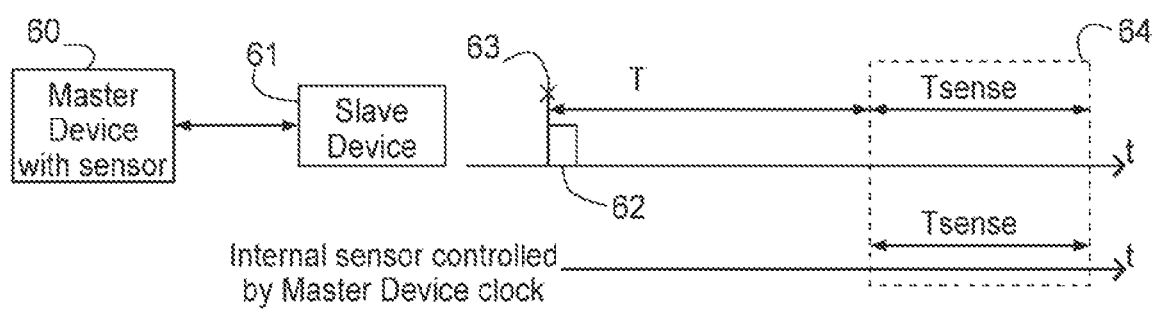
FIG. 8 illustrates an embodiment with one sensor device to be synchronized with the master device according to one embodiment of the invention FIG. 9 schematically illustrates a system according to one embodiment of the invention for harvesting EEG signal from a wearable EEG monitoring module to a master device.

FIG. 8 illustrates an embodiment with one sensor device to be synchronized with the master device according to one embodiment of the invention. At least one sensor device, here slave device 61, is wirelessly connected to a master device 60. The master device 60 is in this embodiment responsible for the timing in the wireless body area network which in this embodiment consists of the slave device 61 having one or more sensors, e.g. a PPG sensor. The master device 60 may be a smartphone and include an accelerometer or other sensors. When processing synchronized sensor signals in the master device 60, the accelerometer signal is used for removing movement artefacts from the PPG signal.

The master device 60 sends a synchronization message 62 to the slave device 61, and the slave device 61 determines upon reception a time anchor point 63 as explained with reference to FIGS. 4 and 5. The slave devices 61 determines the duration, Tsense, of a sensing period 64, and the time, T, from the time anchor point 63 to the start of the sensing period 64. The master device uses the time, T, for activating its own sensor.

The slave device 61 captures a sensor signal representing physiologic parameters and packetizes the captured sensor signals into payload of one or more data packets 33 (FIG. 3). In this embodiment, the slave device 61 may have a unique ID. The unique ID is not necessarily necessary for the synchronization message 62 but may be valuable for signal encryption. Resynchronization of the sensor may be required from time to time.

Depending on the monitored physiologic signal, the sensor devices need to be synchronized, and when e.g. an EEG signal is monitored in a multi-sensor mesh, is has been observed that the origin and expansion of seizures can be detected when the sensors in the multi-sensor mesh are synchronized within 100 μsec. In one embodiment, the sensors are synchronized within 25 μsec. This is achievable when the data-rate of the Sync-word is 40 kbit per second or higher and the slave device 61.1-61.N avoids introducing individual delays in reading the Sync-word.

Figure 12:
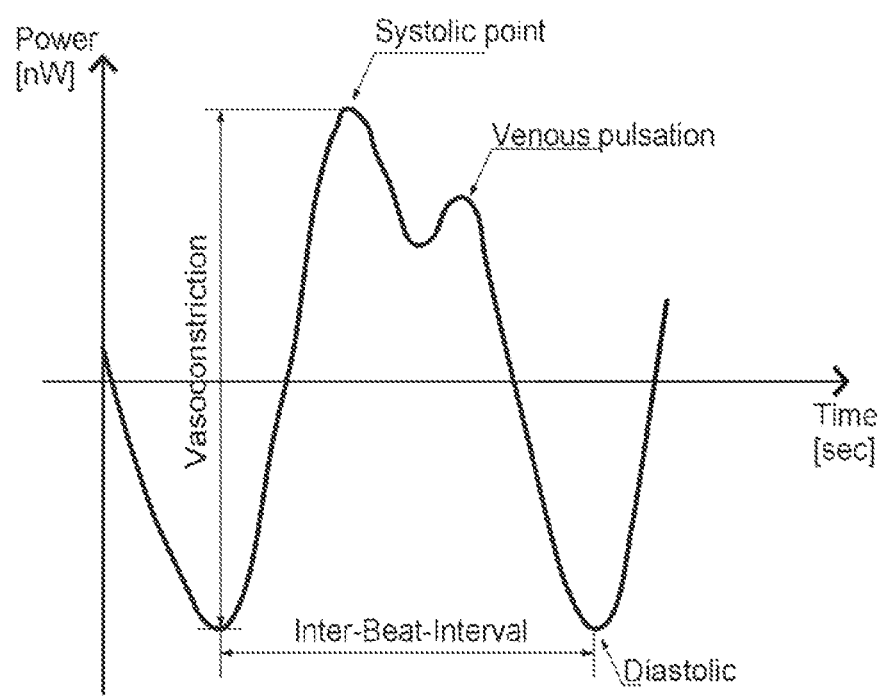
FIG. 12 illustrates a heartbeat signal.

FIG. 12 illustrates a pulse signal captured by a PPG sensor. Light produced by a green and a red LED is directed toward the skin and are absorbed by the blood. Portion of the light is reflected and captured by a photo detector.

The light originating from the green LED contains most of the information on the pulse wave (i.e., the heartbeat) and it is typically characterized by a sequence of valleys used to estimate the heartbeat. It is worth noticing that oxygenated blood absorbs more light. The light originating from the red LED contains a reference light level which often is used to suppress motion artefacts.

The PPG signal shown in FIG. 12 is a periodic pulse signal having local minima called diastolic points used to compute an Inter-Beat-Interval. The periodic pulse signal has furthermore local maxima called systolic points that can be used in conjunction with the diastolic point to estimate the vasoconstriction of the object. A dicrotic notch may be observed between the systolic point and the venous pulsation, and this can be used to study different types of cardiac diseases.

The difference of the PPG signal at the systolic point and the diastolic point is basically the difference in reflected light between the most and least oxygenated blood condition. When the sensor is correct positioned, and the influence of motion is removed, this difference in light gives an information on the vasoconstriction of object.

Figure 9:
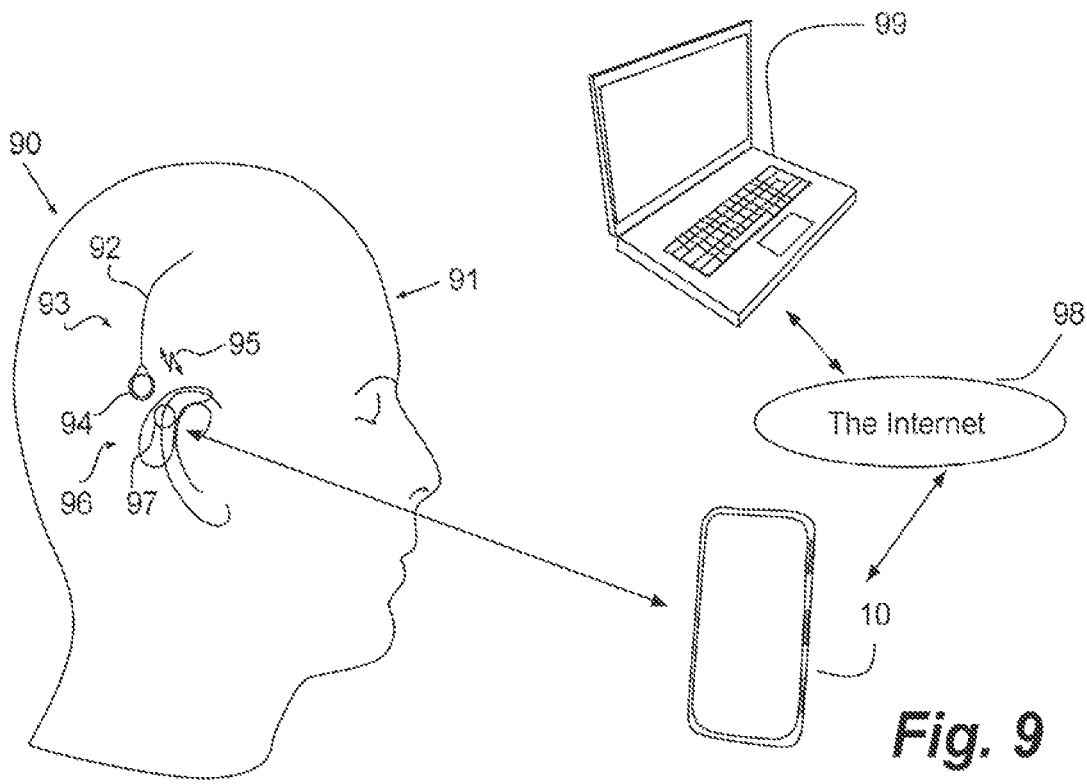

Reference is made to FIG. 9, which schematically illustrates a system for harvesting sensor data from at least one sensor device to a master device. The least one sensor device is in the illustrated embodiment a wearable EEG monitoring module 90. For some purposes the user may wear one wearable EEG monitoring module 90 at each ear.

The wearable EEG monitoring module 90 may be adapted for remote surveillance of an EEG signal. The person being monitored wears the wearable EEG monitoring module 90 comprising an implantable EEG sensor 93 and an associated processing unit 96. The implantable EEG sensor 93 and the processing unit 96 are adapted to be in wireless communication 95 through the skin of the person. The implantable EEG sensor 93 comprises electrodes 92. The Implantable EEG sensor 93 will have at least two electrodes 92, which may be arranged as separate electrodes along the same wire as illustrated. One wire comprising all electrodes associated with respective conductors may facilitate the implantation process. The Implantable EEG sensor 93 is adapted for implantation on the head 91. This implantation may be subcutaneous or intra cranial. The advantage is that a better contact between electrodes and tissue can be obtained. A subcutaneous EEG sensor can also be implanted relatively easy.

The implantable EEG sensor 93 is provided with an electronic module 94 receiving one or more differential EEG signals from at least two electrodes 92. The processing unit 96 is preferably arranged at the ear of the person of whom the EEG signal is being monitored. Preferably, the processing unit 96 is arranged in a housing behind the ear. This also facilitates a position as close as possible to the implanted part, which is important for the wireless communication and power transfer through the skin.

The wearable EEG monitoring module 90 communicates preferably with the personal communication device 10—here shown as a smartphone—by means of the Bluetooth Low Energy protocol. The personal communication device 10 according to the invention is Internet enabled which means that the personal communication device 10 may access the Internet 98 via a wireless Internet connection (e.g. WLAN), or a cellular data connection.

The implantable EEG sensor 93 is via an inductive coupling 95 in communication with the processing unit 96. This inductive coupling 95 is applied to transfer power from the processing unit 96 to the implantable EEG sensor 93. Thereby, it is possible to operate the implantable EEG sensor 93 without a battery. In one embodiment, the implantable EEG sensor 93 is connected to the processing unit 96 via wires.

A server 99 hosts a centrally operated out-patient Electronic Medical Record (EMR) system or an electronic patient medical database being accessible over the Internet. Each patient record may involve remote surveillance of an EEG signal. This includes a unique identity for an associated EEG monitoring module 90.

In one embodiment, the user has two wearable EEG monitoring modules 90 acting as sensor devices according to the invention. The personal communication device 10 sends synchronization messages (FIG. 4, step 40) to the two wearable EEG monitoring modules 90, start to capture synchronized sensor signals, e.g. differential EEG signals. The synchronized sensor signals are transmitted to the personal communication device 10, where the captured synchronized sensor signals are processed, or passed via the internet 98 to the server 99 for processing the captured synchronized sensor signals. It is important that captured sensor signals are still synchronized when processed. The personal communication device 10 and/or the server 99 are adapted to offer control elements, display alarm (together with an acoustic alarm), and present logged data.

When a medical professional or a monitoring server needs to exchange or collect data from the wearable EEG monitoring module 1, the patient medical record may be accessed in the patient record server 99 from where the unique identity for the EEG monitoring module in question may be retrieved. The personal communication device 10 operates as master device regarding sensor synchronization. The centrally operated out-patient Electronic Medical Record (EMR) system or an electronic patient medical database contains personal information such as name, address and additional contact data like phone number and e-mail address.

Electroencephalography (EEG) is an electrophysiological monitoring method to record electrical brain activity. When the electrodes placed along the scalp, the method is called noninvasive. The method illustrated with reference to FIG. 9 uses invasive electrodes. EEG measures voltage fluctuations resulting from ionic current within the neurons of the brain. The EEG signal represents the brain's spontaneous electrical activity over time. Often multiple electrodes are arranged in a mesh arranged on the scalp.

The EEG is typically a combination of rhythmic activity and transients. The rhythmic activity is divided into bands by frequency. The rhythmic activity for certain frequency ranges has been observed to have a certain distribution over the scalp or a certain biological significance. The major part of the cerebral signal observed in the scalp EEG is within the frequency range of 1-20 Hz, and the Waveforms are subdivided into bandwidths known as alpha, beta, theta, and delta. The type of neural oscillations ("brain waves") that can be observed in EEG signals in the frequency domain.

EEG may be used to e.g. diagnose epilepsy or monitoring hypoglycemia (low blood sugar), both causing abnormalities in EEG readings. EEG is a valuable tool for research and diagnosis as it is a mobile technique offering temporal resolution.

The embodiment explained with reference to FIG. 9 may be used for monitoring patients having epileptic seizures and for picking up EEG data for analyzing seizure expression, behavior (including origin prediction and monitoring whether the seizure becomes generalized), and brain morphology differences. By adding additional sensor devices prepared for synchronization orchestrated by a master device, a multi-site EEG sensor device mesh may be set upon allowing the patient to be monitored while his normal behavior is maintained.

Furthermore, multiple synchronized channels will allow a better clean up the signals (signal processing) due to more information e.g. by using blind "source separation" or "independent component analysis". Seizures may be clearer in one or more sensor due to its origin, and expansion can be observed. It will be possible to monitor both right and left temporal lobe simultaneously.

A multi-site EEG mesh of synchronized sensor device offers significant potential for data mining, including deep learning. In one embodiment useful in a medical care center, at least two EEG monitoring modules 90 are coupled via the master device 10 to a powerful computer 99 responsible for the deep learning calculations. In one embodiment, the master device 10 extracts some physiological parameters, while the computer 99 extracts other physiological parameters for the deep learning calculations.

For capturing physiologic EEG signals, the intended use of the signal specifies the required sample rate. In some embodiments, the EEG signal has very high temporal resolution, on the order of milliseconds. EEG may be recorded at sampling rates between 250 and 2000 Hz which is like clinical and research settings. However, for some purposes EEG data collection systems may record at sampling rates above 20 kHz. Raw data recorded at 2 kHz with a 24-bit sample size requires a data acquisition rate at 48 kbit/second. To minimize data buffering, this is the required data bandwidth between the EEG monitoring module 90 and the master device 10.

Figure 10:
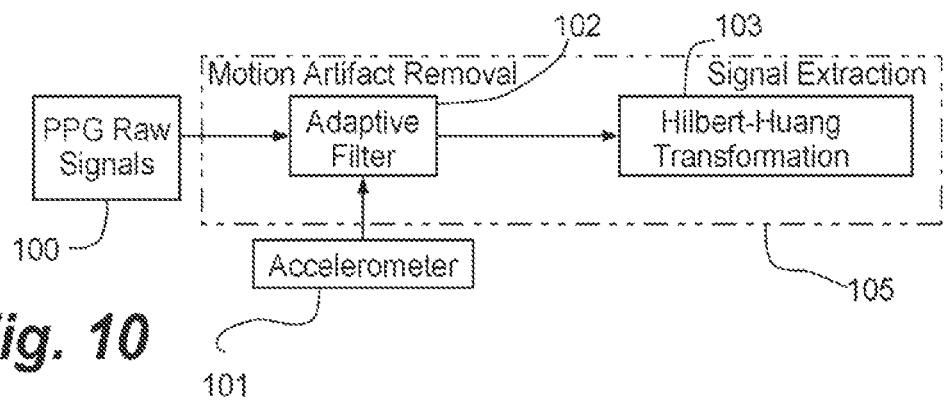
FIG. 10 illustrates an embodiment according to the invention for removing motion artefacts from PPG signals.
Figure 11:
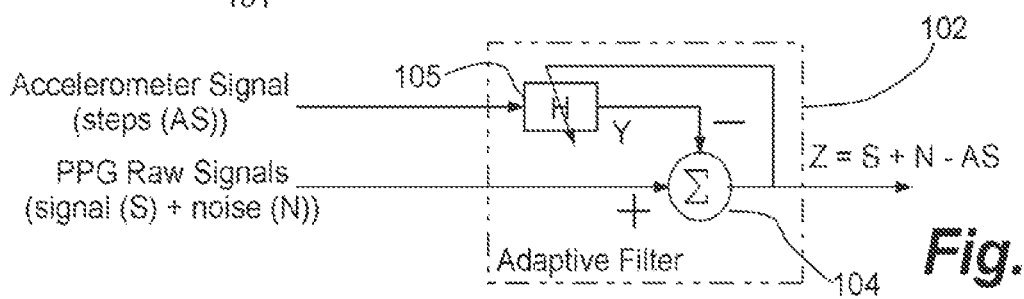
FIG. 11 illustrates in detail the operation of the adaptive filter for motion artefacts removal shown in FIG. 10.

FIGS. 10 and 11 illustrates a method according to the invention for removing motion artefacts from PPG signals. A PPG Raw signal 100 received from a plurality of Slave Devices (e.g. the hearing aids 13 and 14 equipped with PPG sensors) and synchronized by the method as explained in FIG. 4. Motion artefacts is in general a problem as it significantly interferes with the desired physiological signals. Using a PPG sensor array capturing the physiological signals at multiple position, e.g. in three slave devices, raw signals are generated and wirelessly transmitted to the master device, e.g. the personal communication device 10, which may be a smartphone. Here the raw signals are amplified, e.g. 10, 100 and 1000-fold for preventing signal saturation (clipping due to over amplification).

In the present embodiment, the personal communication device 10 includes a triaxial accelerometer 101, and the output signal of a triaxial accelerometer 101 is applied to an adaptive filter 102 as a reference to remove motion artefacts.

The motion artefact removal stage in a processor 105 is designed to remove motion artefacts using an adaptive filter 102. The raw signal 100, decomposed into a desired PPG signals, S, and inherent noise, N, is applied to an input of the adaptive filter 102, and the output signal of a triaxial accelerometer 101, here seen as noise, AS, is applied to the other input of the adaptive filter 102. The output signal, AS, of a triaxial accelerometer 101 will often represent steps of the user carrying the Slave Devices (e.g. the hearing aids 13 and 14) why AS often will be substantially correlated with the noise, N, but not with the signal, S, and applicable for removing the motion artefacts.

After the motion artefacts have been substantially removed from the PPG signal, S, by the adaptive filter 102, the PPG signal, S, is passed to a signal extraction unit in the processor 105, where a Hilbert-Huang transform (HHT) may be used for obtaining instantaneous frequency data by decomposing the PPG signal, S, into so-called Intrinsic Mode Functions along with a trend. The Hilbert-Huang transform (HHT) is designed to work well for data that is nonstationary and nonlinear. Then the instantaneous frequency data may be used for monitoring heart activity, pulse, blood pressure, etc., depending on where the sensors are positioned on the body of the monitored user.

The operation of the adaptive filter 102 is illustrated in FIG. 11. The output signal, AS, from the triaxial accelerometer 101, is used to remove the motion artefacts in a linear filter 105 having a transfer function, H, controlled by variable parameters. The linear filter 105 has an output Y determined by the transfer function H. The desired PPG signal may be defined as output, Z=S+N−AS. As the motion artefacts is time-dependent, the filter must be adaptive, using the output Z as a feedback signal for the linear filter 105 to control the transfer function, H.

The invention claimed is:

1. A monitoring system comprising a master device adapted for wireless communication with two slave devices each having a sensor adapted for acquiring a respective physiological signal,
wherein the master device is adapted for
providing synchronization signals to the two slave devices, and
instructing each of the two slave devices to acquire the respective physiological signal based on timing instructions,
wherein each of the two slave devices is adapted for
receiving a synchronization message,
setting a time anchor point based on the synchronization message,
measuring the respective physiological signal by means of the sensor according to the received timing instructions at a predetermined point of time relative to the time anchor point that is the same for each of the two slave devices so as to synchronize measurement of the respective physiological signals between the two slave devices, and
transmitting the acquired respective physiological signal wirelessly to the master device, and
wherein the master device comprises a processor adapted for processing the acquired physiological signals acquired by the sensors of at least two slave devices in order to extract a measure for a physiological parameter.

2. The monitoring system according to claim 1, wherein the two slave devices are embodied by a set of hearing aids.

3. The monitoring system according to claim 1, wherein each of the two slave devices is adapted to encode the respective acquired physiological signal into digitized data packets and transmit the data packets to the master device.

4. The monitoring system according to claim 3, wherein each of the two slave devices is adapted to include timing metadata in the digitized data packets transmitted to the master device.

5. The monitoring system according to claim 1, wherein the master device is adapted to
receive digitized data packets from the two slave devices,
decode the received digitized data packets to identify sensor data and timing metadata, and
process the received sensor data received from the two slave devices in the processor to extract physiologic characteristics from the sensor data.

6. The monitoring system according to claim 1, wherein the processor is adapted for processing the physiological signals acquired by sensors present in the two slave devices and a further sensor present in the master device.

7. The monitoring system according to claim 1, wherein the processor is adapted for processing the physiological signals acquired by a first sensor present in one of the two slave devices and a second sensor present in the other of the two slave devices.

8. The monitoring system according to claim 1, wherein the processor is adapted for applying an adaptive filter for removing noise from the physiological signals acquired by the sensors of the two slave devices.

9. The monitoring system according to claim 1, wherein one of at least two slave devices includes one photoplethysmogram (PPG) sensor using a pulse oximeter illuminating the skin and measuring changes in light absorption.

10. The monitoring system according to claim 1, wherein one of at least two slave devices includes one electrode for sensing an electroencephalography (EEG) signal from an ear canal of a user of the hearing aid.

11. The monitoring system according to claim 1, wherein the at least one slave device is a wearable electroencephalography (EEG) monitoring module adapted for remote surveillance of an EEG signal.

12. A method of operating a monitoring system comprising a master device adapted for wireless communication with two slave devices each having a sensor adapted for acquiring a respective physiological signal, wherein the method comprises steps of,
providing synchronization signals to the two slave devices by the master device,
instructing the two slave devices to acquire the respective physiological signal based on timing instructions for synchronization by the master device,
receiving a synchronization message by the two slave devices,
setting a time anchor point based on the synchronization message by the two slave devices,
measuring the respective physiological signal by means of the respective sensor according to the received timing instructions by each of the two slave devices at a predetermined point of time relative to the time anchor point that is the same for each of the two slave devices so as to synchronize measurement of the respective physiological signals between the two slave devices, transmitting the acquired physiological signal wirelessly from the at least two slave device to the master device, and processing in the master device the physiological signals acquired by the sensors in the two slave devices in order to extract a measure for a physiological parameter.

13. The method according to claim 12, wherein each of the at least two slave devices is adapted to include timing metadata accompanying the acquired physiological signal transmitted to the master device.

\* \* \* \* \*